United States Patent [19]

Bingmann

[11] Patent Number: 4,508,904
[45] Date of Patent: Apr. 2, 1985

[54] FLUORANE COMPOUNDS

[75] Inventor: Horst Bingmann, Hofheim am Taunus, Fed. Rep. of Germany

[73] Assignee: Hoechst Aktiengesellschaft, Fed. Rep. of Germany

[21] Appl. No.: 492,822

[22] Filed: May 9, 1983

[30] Foreign Application Priority Data

May 18, 1982 [DE] Fed. Rep. of Germany ....... 3218645

[51] Int. Cl.$^3$ .......................................... C07D 493/10
[52] U.S. Cl. .................................................. 546/196
[58] Field of Search ................................ 546/187, 196

[56] References Cited

U.S. PATENT DOCUMENTS 3,901,918 8/1975 Koga et al. ........................... 260/335

FOREIGN PATENT DOCUMENTS 2422899 12/1974 Fed. Rep. of Germany .

Primary Examiner—Norma S. Milestone
Attorney, Agent, or Firm—Connolly and Hutz

[57] ABSTRACT

Fluorane compounds of the formula (1)

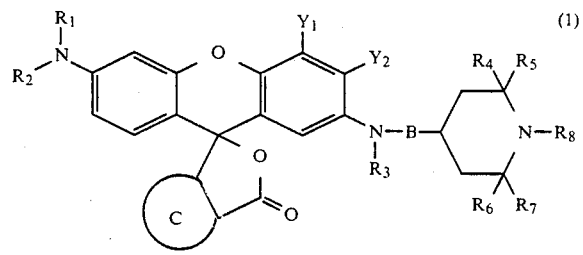

in which each of $R_1$ and $R_2$ is an H atom or an alkyl$_{C_1-C_{12}}$, cycloalkyl$_{C_5-C_7}$, alkenyl$_{C_2-C_4}$, phenyl, naphthyl or benzyl group and $R_1$ and $R_2$, together with the N atom, can be an optionally alkyl$_{C_1-C_4}$-substituted piperidine or morpholine radical, $R_3$ represents an H atom or an alkyl$_{C_1-C_{12}}$, cycloalkyl$_{C_5-C_7}$, alkenyl$_{C_2-C_4}$, phenyl, naphthyl, benzyl, acetyl, propionyl or benzoyl group, each of $R_4$, $R_5$, $R_6$ and $R_7$ denotes an alkyl$_{C_1-C_4}$ group, $R_8$ is an H atom or an alkyl$_{C_1-C_4}$, benzyl, acetyl, propionyl or benzoyl group, each of $Y_1$ and $Y_2$ represents a hydrogen, fluorine, chlorine or bromine atom or an alkyl$_{C_1-C_4}$, alkoxy$_{C_1-C_4}$, nitro, optionally alkyl$_{C_1-C_4}$-substituted amino, phenyl, naphthyl or benzyl group, and $Y_1$ and $Y_2$ together can be the radical —CH=CH—CH=CH— or the n-butylene radical, B is a direct bond or an alkylene$_{C_1-C_6}$ or alkenylene$_{C_3-C_6}$ group, C is a 1,2-phenylene, 1,2-naphthylene, 2,3-naphthylene or 1,8-naphthylene radical and $Y_2$ and $R_3$ together can be an optionally alkyl$_{C_1-C_4}$-substituted alkylene$_{C_2-C_3}$ or alkenylene$_{C_2-C_3}$ radical, where each of $R_1$, $R_2$, $R_3$, $R_8$, $Y_1$, $Y_2$, B and C provided they do not represent a direct bond, a hydrogen, chlorine or bromine atom or a nitro group can be substituted independently of one another by fluorine, chlorine or bromine atoms, hydroxyl, alkoxy$_{C_1-C_4}$, nitro optionally alkyl$_{C_1-C_4}$-substituted amino, cyano, acetyl, propionyl, optionally alkyl$_{C_1-C_4}$-substituted carboxamide, carboxyl or carb(alkoxy$_{C_1-C_4}$) groups, processes for their preparation, and their use as color formers in a pressure- or heat-sensitive recording material.

3 Claims, No Drawings

FLUORANE COMPOUNDS

The invention relates to new fluorane compounds of the general formula (1)

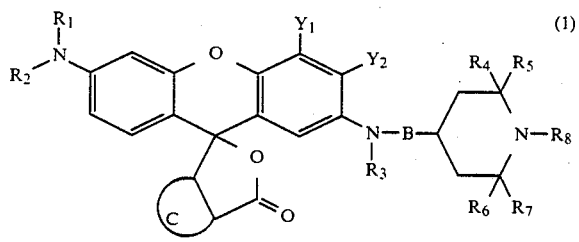

in which each of $R_1$ and $R_2$ independently of each other denotes a hydrogen atom or a straight-chain or branched alkyl$_{C_1-C_{12}}$, cycloalkyl$_{C_5-C_7}$, alkenyl$_{C_2-C_4}$, phenyl, naphthyl or benzyl group and $R_1$ and $R_2$, together with the nitrogen atom, can represent an optionally alkyl$_{C_1-C_4}$-substituted piperidine or morpholine radical, $R_3$ represents a hydrogen atom or an alkyl$_{C_1-C_{12}}$, cycloalkyl$_{C_5-C_7}$, alkenyl$_{C_2-C_4}$, phenyl, naphthyl, benzyl, acetyl, propionyl or benzoyl group, each of $R_4$, $R_5$, $R_6$ and $R_7$ independently of one another denotes an alkyl$_{C_1-C_4}$ group, $R_8$ represents a hydrogen atom or an alkyl$_{C_1-C_4}$, benzyl, acetyl, propionyl or benzoyl group, each of $Y_1$ and $Y_2$ independently of each other represents a hydrogen, fluorine, chlorine or bromine atom or an alkyl$_{C_1-C_4}$, alkoxy$_{C_1-C_4}$, nitro, optionally alkyl$_{C_1-C_4}$-substituted amino, phenyl, naphthyl or benzyl group, and $Y_1$ and $Y_2$ together can represent the radical —CH=CH—CH=CH— or the n-butylene radical, B denotes a direct bond or a straight-chain or branched alkylene$_{C_1-C_6}$ or alkenylene$_{C_3-C_6}$ group, C represents a 1,2-phenylene, 1,2-naphthylene, 2,3-naphthylene or 1,8-naphthylene radical and $Y_2$ and $R_3$ together can be an optionally alkyl$_{C_1-C_4}$-substituted alkylene$_{C_2-C_3}$ or alkenylene$_{C_2-C_3}$ radical, where each of $R_1$, $R_2$, $R_3$, $R_8$, $Y_1$, $Y_2$, B and C provided they do not represent a direct bond, a hydrogen, fluorine, chlorine or bromine atom or a nitro group can be substituted independently of one another by fluorine, chlorine or bromine atoms, hydroxyl, alkoxy$_{C_1-C_4}$, nitro or optionally alkyl$_{C_1-C_4}$-substituted amino, cyano, acetyl, propionyl, optionally alkyl$_{C_1-C_4}$-substituted carboxamide, carboxyl or carb-(alkoxy$_{C_1-C_4}$) groups, to processes for their preparation, and to their use as color formers in a pressure- or heat-sensitive recording material.

Particularly valuable fluorane compounds of the abovementioned general formula (1) are those of the general formula (2)

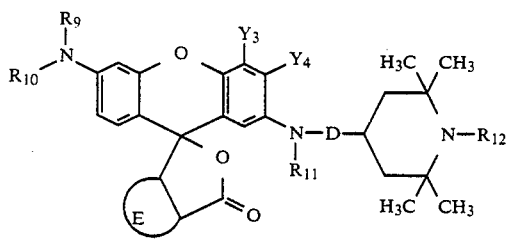

in which each of $R_9$ and $R_{10}$ independently of each other denotes a hydrogen atom or an alkyl$_{C_1-C_4}$ or benzyl group, each of $R_{11}$ and $R_{12}$ independently of each other denotes a hydrogen atom or an alkyl$_{C_1-C_4}$, benzyl, acetyl, propionyl or benzoyl group, each of $Y_3$ and $Y_4$ independently of each other denotes a hydrogen, chlorine or bromine atom or an alkyl$_{C_1-C_4}$, alkoxy$_{C_1-C_4}$, phenyl or naphthyl group, provided that one of $Y_3$ and $Y_4$ is hydrogen if the other of these two substituents is not hydrogen, D denotes a direct bond or the 1,2-ethylene group and E denotes the optionally chlorine- or bromine-substituted 1,2-phenylene radical.

Fluorane compounds of the said formulae (1) and (2) can be prepared by methods known per se. For instance, the new compounds of the said formula (1) can be prepared by reacting a carboxylic acid of the general formula (3)

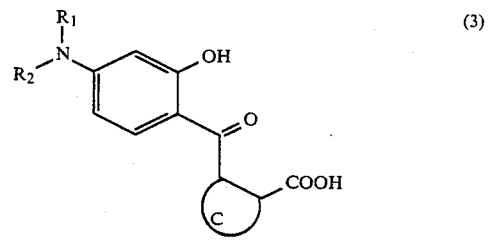

in which $R_1$, $R_2$ and C have the abovementioned meanings, with a p-aminophenol compound of the general formula (4)

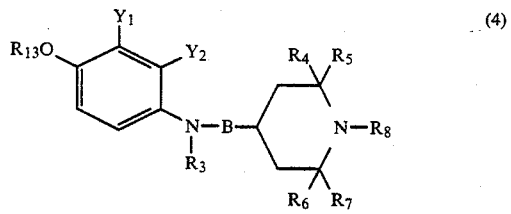

in which $R_{13}$ represents a hydrogen atom or an alkyl$_{C_1-C_4}$, acetyl, propionyl or benzoyl group, and $R_3$, $R_4$, $R_5$, $R_6$, $R_7$, $R_8$, $Y_1$ and $Y_2$ have the abovementioned meanings, in the presence of a dehydrating condensing agent, such as, for example, sulfuric acid or phosphoric acid, at temperatures of about 10° to about 200° C., preferably about 50°–about 150° C. The reaction takes 1 to 20 hours, depending on the reaction temperature used and on the starting reactants.

The compounds of the said general formulae (3) and (4) can be used in a molar ratio of 1:1. However, it can be advantageous to use one of the two components in an excess of up to about 100 mole percent.

On completion of the reaction the reaction mixture is hydrolyzed by pouring it onto ice-water and subsequently neutralizing the mixture by adding a base, such as, for example, sodium hydroxide solution or ammonia, filtering off the precipitated solid or extracting with a water-immiscible inert organic solvent, such as, for example, toluene, and, if appropriate after the solvent has been drawn off, purifying the formula (1) compound obtained by recrystallizing it in a suitable solvent. Examples of solvents suitable for the recrystallization are toluene, halogenated hydrocarbons, alcohols, aliphatic hydrocarbons and ethers.

The new compounds of the said formula (1) can also be prepared by, for example, reacting a fluorine compound of the general formula (5)

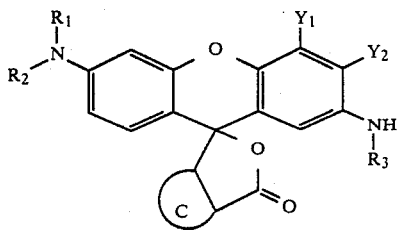

(5)

in which $R_1$, $R_2$, $R_3$, $Y_1$, $Y_2$ and C have the above-mentioned meanings, if appropriate in the presence of a dehydrating agent, such as, for example, sulfuric acid or phosphoric acid or of a dehydrohalogenating agent, such as, for example, an inorganic base, such as potassium carbonate or sodium carbonate, or of an organic base, such as pyridine or triethylamine, with a compound of the general formula (6)

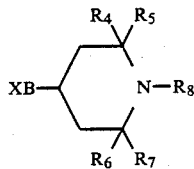

(6)

in which X represents a chlorine, bromine or iodine atom or a hydroxyl, acetyl or sulfonyl group, and $R_4$, $R_5$, $R_6$, $R_7$, $R_8$ and B have the abovementioned meanings, in an inert organic solvent, such as, for example, toluene, cyclohexane or dimethylformamide, at temperatures of about 20° to 200° C., preferably of about 80° to about 150° C.

The compounds of the said general formulae (5) and (6) can be used in a molar ratio of 1:1. However, it can be advantageous to use one of the two components in an excess of up to about 100 mole percent.

On completion of the reaction the reaction mixture is hydrolyzed by pouring it onto ice-water. The resulting mixture is then neutralized by adding a base, such as, for example, sodium hydroxide solution or ammonia, the precipitated solid is filtered off, or the mixture is extracted with a water-immiscible solvent, such as, for example, toluene, and the formula (1) compound obtained is purified, if appropriate after the solvent has been drawn off, by recrystallization in a suitable solvent.

The new fluorane compounds of the invention are generally colorless compounds which are very suitable for use as color formers in pressure- or heat-sensitive recording materials. Brought into contact with an acid reactive substance, i.e. an electron acceptor, they rapidly develop a blue, green, red or black color, the preferred compounds of the formula (2) a strong grey to black color. Typical examples of the acid co-reactants generally used in the carbon-free copying systems are bentonites, attapulgus clay, silicon dioxide, aluminum oxide, kaolin and an acidic polymeric material, such as, for example, a phenol-formaldehyde resin. The new fluorane compounds are colorless and readily soluble in the non-volatile solvents customarily used for preparing carbon-free copying systems, and are insoluble in water. They give very compatible mixtures with other color formers. The tetraalkylpiperidine-substituted fluorane compounds of the invention have a significantly better light fastness than the fluorane compounds described in German Offenlegungsschrift No. 2,422,899 and in German Offenlegungsschrift No. 2,253,161.

The new fluorane compounds are highly suitable for use as chromogenic electron donors (color formers) for a large number of carbon-free pressure-sensitive copying systems of the type described, for example, in U.S. Pat. Nos. 2,712,507, 2,730,457, 2,932,582, 3,418,250, 3,418,656, 3,427,180, 3,516,846 and 3,672,935 and in British Pat. Nos. 1,042,596–1,042,599, 1,053,935 and 1,517,650.

They are also highly suitable for use as color formers for thermoreactive recording materials of the type described, for example, in German Offenlegungsschrift No. 2,110,854 and German Offenlegungsschrift No. 2,228,581, French Pat. No. 1,524,826 and Swiss Pat. Nos. 407,185, 444,196 and 444,197.

The following examples are intended to illustrate the invention in more detail without, however, restricting it to their subject matter. In the examples, parts are by weight.

EXAMPLE 1

A mixture of 31.3 parts of 2-(2'-hydroxy-4'-diethylaminobenzoyl)-benzoic acid, 27.6 parts of 4-(1',2',2',6',6'-pentamethylpiperidin-4'-yl)-aminoanisole and 150 parts of sulfuric acid monohydrate is stirred at 80° C. for 5 hours, and then poured onto 1,500 parts of ice-water. The mixture is neutralized with aqueous sodium hydroxide solution, and the precipitate formed is filtered off, washed with water and recrystallized in a toluene/petroleum ether mixture.

This gives 35 parts of the compound of the formula

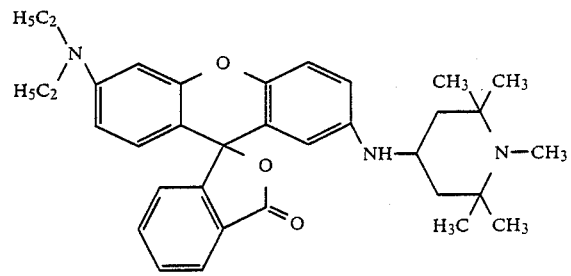

in the form of colorless crystals which melt at 153° C. A solution of this compound in acetone/water (80:20) which has been adjusted to pH 3 has maxima in the UV-visible spectrum at 425, 450 and 586 nm. A solution of the compound in a toluene solution is colorless and gives a black color on silicon oxide, a greenish black color on bentonite and a dark green color on phenolic resin.

EXAMPLE 2

40.0 parts of 2-amino-3-methyl-6-diethylamino-fluorane and 20.4 parts of 1-(2',2',6',6'-tetramethyl-piperidin-4'-yl)-2-chloroethane are held at 80°–90° C. for 5 hours in 50 parts of N,N-dimethylformamide to which 10 parts of sodium carbonate have been added. The reaction mixture is then poured onto ice-water. The mixture obtained is extracted with toluene, and the extract is washed with dilute aqueous sodium hydroxide solution and water, and dried with sodium sulfate.

The solvent is evaporated off to give the compound of the formula

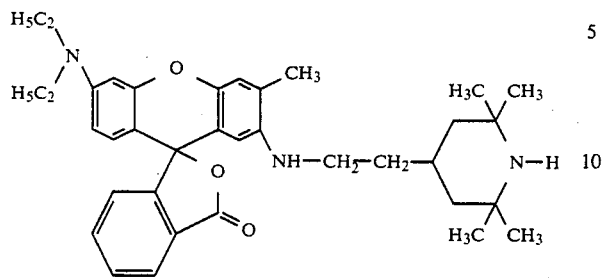

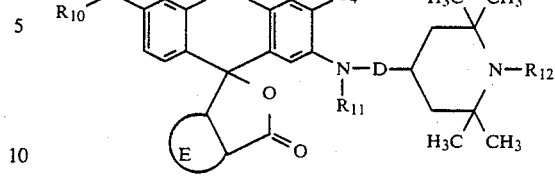

in the form of colorless crystals. The colorless solution of the compound in toluene gives a black color on silicon dioxide, a greenish black color on bentonite and a dark green color on phenolic resin.

The new fluorane compounds of the general formula (1) which are listed in the table below can be prepared in analogy to Examples 1 and/or 2 by the methods described above.

in which:

$R_9$ and $R_{10}$ independently of each other each denote an alkyl group having 1–4 carbon atoms or a benzyl group;

$R_{11}$ and $R_{12}$ independently of each other each denote a hydrogen atom, an alkyl group having 1 to 4 carbon atoms, or a benzyl, acetyl, propionyl or benzoyl group;

$Y_3$ denotes a hydrogen chlorine, or bromine atom, an alkoxy group having 1 to 4 carbon atoms, or a phenyl group;

$Y_4$ denotes a hydrogen atom or an alkyl or alkoxy group having 1 to 4 carbon atoms; provided, that one of $Y_3$ and $Y_4$ is hydrogen, if the other of these two substituents is not hydrogen;

D denotes a direct bond or the 1,2-ethylene group; and

E denotes a 1,2-phenylene radical, unsubstituted or substituted with chlorine or bromine.

TABLE

| Example | $R_1=R_2$ | $R_3$ | $R_8$ | $Y_1$ | $Y_2$ | B | C | Color |
|---|---|---|---|---|---|---|---|---|
| 3 | $C_2H_5$ | H | $COCH_3$ | H | H | direct bond | (o-tolyl) | black |
| 4 | $CH_3$ | $COCH_3$ | $COCH_3$ | H | H | " | " | dark red |
| 5 | $CH_2$–Ph | H | $CH_3$ | H | $CH_3$ | " | " | black |
| 6 | $C_2H_5$ | $CH_2$–Ph | H | Ph | H | " | " | green |
| 7 | $C_2H_5$ | $CH_3$ | H | $OC_2H_5$ | H | " | " | green |
| 8 | $C_2H_5$ | $C_2H_5$ | H | H | H | $-CH_2-CH_2-$ | " | dark green |
| 9 | $CH_3$ | H | $CH_2$–Ph | H | H | $-CH_2-CH_2-$ | " | black |
| 10 | $C_2H_5$ | H | $C_2H_5$ | H | $C_2H_5$ | $-CH_2-CH_2-$ | (tetrachlorophenyl) | black |
| 11 | $C_2H_5$ | $CH_3$ | $CH_3$ | Cl | H | $-CH_2-CH_2-$ | (o-tolyl) | dark green |
| 12 | $C_2H_5$ | H | H | H | $OCH_3$ | $-CH_2-CH_2-$ | " | violet-tinged black |

I claim:

1. A fluorane compound of the formula (2)

2. The fluorane compound of the formula

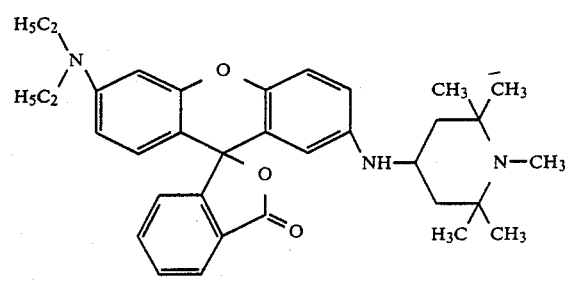
3. The fluorane compound of the formula
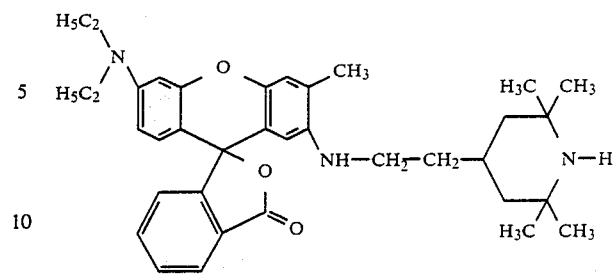
* * * * *